United States Patent
Amirana

[11] Patent Number: 5,897,531
[45] Date of Patent: Apr. 27, 1999

[54] ADHESIVE SURGICAL RETAINING DEVICE

[76] Inventor: Omar Amirana, 883 Payne Ct., Sunnyvale, Calif. 94087

[21] Appl. No.: 08/669,583

[22] Filed: Jun. 24, 1996

Related U.S. Application Data

[63] Continuation of application No. 08/178,538, Jan. 7, 1994, abandoned.

[51] Int. Cl.⁶ .................................... A61M 5/32
[52] U.S. Cl. .................................... 604/180; 128/DIG. 26
[58] Field of Search .................................... 604/180, 174, 604/177; 128/DIG. 26

[56] References Cited

U.S. PATENT DOCUMENTS

| | | | |
|---|---|---|---|
| 3,957,048 | 5/1976 | Jacobs | 604/180 |
| 4,419,094 | 12/1983 | Patel | 604/180 |
| 4,579,120 | 4/1986 | MacGregor | 604/174 |
| 5,073,169 | 12/1991 | Raiken | 604/180 |
| 5,137,520 | 8/1992 | Maxson et al. | 604/180 |
| 5,176,648 | 1/1993 | Holmes et al. | 604/180 |
| 5,215,531 | 6/1993 | Maxson et al. | 604/180 |
| 5,263,939 | 11/1993 | Wontrich | 604/180 |
| 5,269,764 | 12/1993 | Vetter et al. | 604/167 |
| 5,279,575 | 1/1994 | Sugarbaker | 604/174 |

*Primary Examiner*—Todd E. Manahan
*Attorney, Agent, or Firm*—Morrison & Foerster LLP

[57] ABSTRACT

This invention is a surgical retainer device for temporarily, but movably, affixing in place, a tube or catheter as it passes through the skin or enters a body cavity. The retainer is adhesively attached to the skin and is constructed in such a way to hold firmly the tube or catheter that penetrates the skin and enters a space within the body. The device may be used to place a medication or ointment at the site of the skin entry. The retainer utilizes a compression or friction fitting which allows the tube or catheter to be moved in or out of the opening through the skin. The device is especially suitable for retaining a chest tube during treatment of pneumothorax although its use is not so limited.

31 Claims, 10 Drawing Sheets

ADHESIVE SURGICAL RETAINING DEVICE

This application is a continuation of application Ser. No. 08/178,538 filed Jan. 7, 1994, now abandoned.

FIELD OF THE INVENTION

This invention is a surgical retainer device for temporarily, but movably, affixing in place, a tube or catheter as it passes through the skin or enters a body cavity. The retainer is adhesively attached to the skin and is constructed in such a way to hold firmly the tube or catheter that penetrates the skin and enters a space within the body. The device may be used to place a medication or ointment at the site of the skin entry. The retainer utilizes a compression or friction fitting which allows the tube or catheter to be moved in or out of the opening through the skin. The device is especially suitable for retaining a chest tube during treatment of pneumothorax although its use is not so limited.

BACKGROUND OF THE INVENTION

In a general sense, there are a variety of indications in medicine in which as a portion of the treatment, the skin is punctured, a body cavity such as the pleural space or peritoneum is accessed by a hollow tube, and a liquid or a gas is introduced into or withdrawn from that body cavity.

The thorax or chest cavity of a person contains the lungs as well the mediastinum which holds both the heart and its associated major vessels. The lungs are in turn contained within a pair of pleural sacs or cavities within the thorax.

Breathing takes place as the chest expands and the lungs are filled with air through the contraction of a variety of inspiratory and expiratory muscles The diaphragm, which is the muscle transecting the body cavity below the pleural spaces, is the principal muscle of inspiration and provides for the movement of more than two-thirds of the air that enters lungs during normal or quiet breathing Contraction of the diaphragm causes its muscular domes to descend and the chest to expand along its length. At the same time, because of vertically oriented attachments of the diaphragm to the rib cage edges, its contractions also elevate the lower ribs. The expiratory muscles are typically those found between the ribs.

It is essential that the pleural sac containing the lungs always be intimately connected with the diaphragm and thoracic walls. Or said another ways if the diaphragm moves and the pleural sac does not, a separation has occurred and the lung does not expand with air. It is this separation that is the condition of pneumothorax. Pneumothorax is the condition where air or other gas is present in at least one of the pleural cavities and therefore prevents expansion of the lung. Pneumothorax occurs for a variety of reasons, including disease, injury to the lung tissue, or puncture of the chest wall. In aggravated circumstances, if the partial vacuum is not restored to the pleural cavities, pneumothorax can eventually be fatal.

There are a number of widely known methods for treating pneumothorax that typically involve introducing a chest tube between a pair of ribs into the pleural cavity having the problem. The tube is usually affixed to the chest wall and connected to a vacuum source for evacuating the chest cavity. This regimen allows the patient to breathe while the cause for the malady is investigated and treated. Although the generic method is widely accepted and practiced, there is no commercial device or specific method which is entirely satisfactory for retaining the chest tube.

There are a variety of ways to hold such an apparatus in place. A classical method involves the simple suturing of the device to the skin. That is to say, a loop of suture thread is passed around the device and that thread is then sewed into the skin at a point near the entry site. Often two such loops are provided to allow better anchoring of the device. Such a practice is typical with tube thoracostomies in which the device is sutured to the skin, packed with gauze, and taped down. However, such an arrangement causes both irritation at the stitch site(s) on the skin and is not failsafe in that it allows slippage of the tube upon movement of the patient. Further, when the tube is to be moved or re-positioned, the stitches, tape, and gauze often must be removed and replaced after movement of the tube is accomplished. The methods using suture and gauze packed with tape are also often problematical in that they are prone to leakage, e.g., in a pneumothorax the suction applied to the tube is by-passed via the leakage at the wound site. In addition, the suture thread, if strained forcefully enough, may tear traumatically through the tissue near the entry site.

Other methods of treating pneumothorax involve the introduction of devices such as are shown U.S. Pat. No. 4,813,941, to Shea. Such device has a large hypodermic needle having elongated shaft and a point for penetrating the skin into the selected pleural cavity. The needle is attached to an exhaustion device having a one-piece outer housing which has a one-way valve for exhausting fluid from the pleural cavity and preventing fluid from returning thereto. The device may have a pair of wings projecting longitudinally from the valve head to allow taping of the device to the human body.

Other methods involve the use of needles inserted into the affected pleural cavity in connection to a vacuum and one-way valve device and even conventional hypodermic syringes.

Another device is shown in U.S. Pat. No. 4382,442, to Jones, which is a pump tube apparatus having valves at each end double walled pump for withdrawing fluids from the pleural cavity upon imposition of suction at the proximal end of the device.

The treatment of hemothoraxe, those instances in which the pleural cavity is filled with blood, is also done by tube thoracostomy. Occasionally, chylothorax, the accumulated of a milky (or chylous) fluid, occurs as a result of cardiovascular surgery, particularly of the great vessels. Some consider the triad of trauma, tuberculosis, and tumor (particularly a lymphoma) as a possible cause of that effect. As a portion of the treatment, the chylothorax is drained and other treatment to transpire. Hemopneumothorax, the presence of blood and air in the pleural space, is also known and is usually caused by trauma, e.g., car accidents, stab wounds, and gunshot wounds.

The other instances in which body cavities are entered by tubing and the like, include peritoneal dialysis, penetration of the walls of the bladder, the stomach, segments of the gastrointestinal tract, or placement of catheters into the cardiovascular systems. Various designs of Trocar are also known in the medical arts.

A wide variety of other devices for holding these drains or tubes in place are known.

U.S. Pat. No. 3,241,554 to Coanda, shows a device for passing through an abdominal wall of a patient to allow peritoneal dialysis to be performed. Specifically, the device involves a pair of coaxial tubes which pass through the peritoneal wall. The two tubes are configured in such a fashion that when the inner tube is pulled in relationship to the outer tube, strips formed of the tubes form wings which bend outward from the tubes and nestle on the inside of the abdominal wall. The two tubes pass through the peritoneal wall and are met at the outside by a set of locking members.

Similarly, U.S. Pat. No. 5,232,453, to Plass et al., shows a catheter holder. The holder has a pad of medical grade adhesive material having one surface for attachment to the skin of a wearer. On the side of the adhesive material opposite the skin may be found a pair of tapes arranged in such a way that the two tapes can be stuck together and also stuck to a catheter which passes through an optional aperture or slit between the tapes. The tape is said to be multiple-use tape so that the catheter may be readjusted as may be found necessary.

U.S. Pat. No. 5,242,415, to Kantrowitz et al., shows a percutaneous access device which is a body of relatively soft, flexible, biocompatible material having a base flange and a projection which projects vertically from the top of the base flange. The upwardly extending body and the base flange each have a bore extending vertically through them. The flange appears to be mounted interior to the skin of a patient and the upward projection is configured in such a way that it easily bends as the tube passing through the device is pulled. The tube is sealed within the device bore only near the bottom end of the bore.

U.S. Pat. No. 4,069,826, to Sessions et al., shows a surgical tube adaptor clamp to facilitate entry of an elongated tube having an outer free curved end suitable for insertion into an opening in a blood vessel or the like. The tube adaptor has flat sidewalls and a bore through which may be placed a length of flexible tubing. The device, after emplacement, passes through a pad 17 which is placed against the skin. The sleeve which enters the body lumen is configured in such a way that it buckles after placement in the blood stream and after retraction of an outer section of the tube. In this way there is efficient seal between the tube and the skin.

U.S. Pat. No. 5,092,850, to Buma, shows a catheter having an adjustable external locking bolster. The external surface of the catheter appears to be threaded to allow adjustment of an external coupling having a locking element which prevents slippage.

U.S. Pat. No. 5,221,265, to List, shows an attachment patch suitable for fastening a variety of medical devices to the human skin. The device includes a carrier material having a pressure sensitive adhesive layer and a protective layer covering the pressure sensitive adhesive The material is cut into fastening strips in such a way that the strips may be lifted from the planar patch and wrapped around a catheter or canula to prevent its movement when inserted through the human skin.

U.S. Pat. No. 5,224,935, to Hollands, shows a catheter retainer having an adhesive pad with projections. The pad is made of a medical grade adhesive material having a hole therethrough. The central circular hole has two members which extend away from the human skin and approximately parallel the catheter access as the catheter exits that hole. Thread may be attached to those members and be wound around the catheter a number of times and tied to the other member.

None of these documents show devices which readily allow adjustment of the tube passing through the skin if and when such movement is necessary.

SUMMARY OF THE INVENTION

This invention is an adhesive surgical retaining device. It is intended to temporarily but movably and reversibly affix in place, a tube or catheter as the tube or catheter passes through the skin. The retainer is generally made up of a flexible planar sheet having adhesive on one side for mounting the device against the skin. The planar field has an aperture through it to allow the passage of the elongated tubular device into the body through the skin. Mounted over the aperture is a fitting. The fitting has an axial passageway to allow the tubing to pass through it and through the planar field or sheet into the human body. Of special interest is a concept that the fitting does not permit the tubing to move unless adjusted to do so.

For instance, the fitting may be a compression sleeve which when twisted and turned compresses the sleeve sufficiently that it denies the tubing the ability to move axially. When twisted the other way, the compression upon the tube lessens and it may be moved with impunity. Other fittings involving interference of fits and the like are also acceptable.

The planar field and the fitting may be any of a wide number of variations. For instance, the planar field may be simple adhesive tape or may be foam-backed adhesive or any of a variety of pliable adhesive backed materials compatible with skin contact. The fitting may extend in a perpendicular fashion from the planar field or at any appropriate or desired angle from the planar field. It is also contemplated that the fitting may swivel so as either to gauge the tubular member passing therethrough or to simply direct that tubing in a desired direction. The planar field may be domed in the region of the aperture to allow packing the wound with such medicaments as antibiotic-bearing petroleum jelly.

The device may be used for a wide variety of indications, e.g., catheters feeding tubes, tubes for peritoneal dialysis, tube thoracostomy, etc. It is especially useful in treating pneumothorax where as a part of the treatment the tubular member may be repositioned and is withdrawn as the lung begins to expand.

This device is significantly improved over the devices used in the past in that it is very quickly applied, it is not so irritating to the patient's skin and there are not so many chances for infection. Because it is easily adjustable, the tendency of an attending physician to use the adjustability is enhanced.

DESCRIPTION OF THE INVENTION

Figure 1:
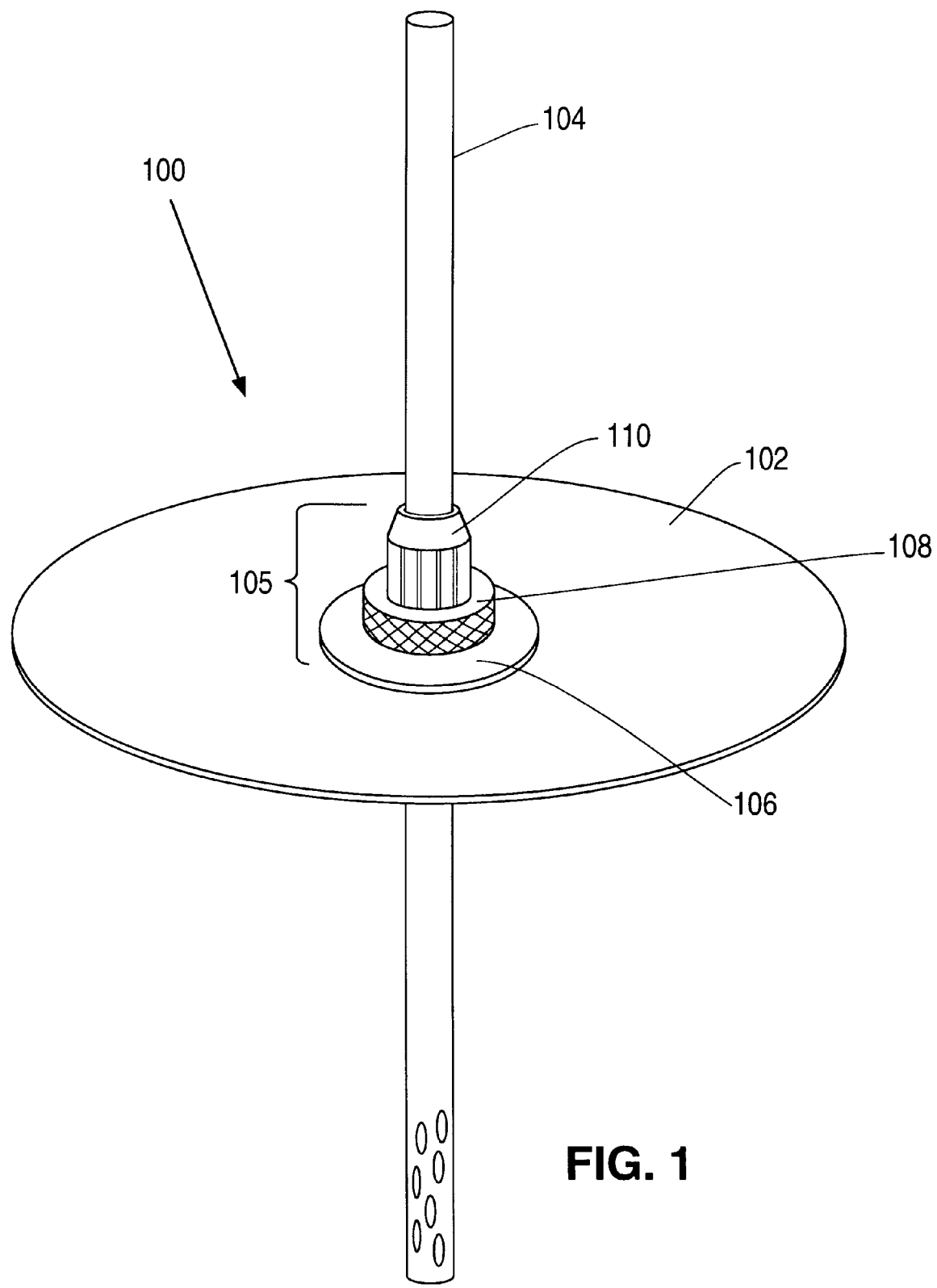
FIG. 1 shows an assembled variation of the inventive device in a front quarter view.

FIG. 1 shows one desirable variation of the inventive retaining device (100). The retaining device (100) is made up of a planar field (102) having an aperture (not shown in this drawing) through which an elongate tube (104) may be placed. The intent of this design and the others discussed herein is simply to allow introduction of the tube (104) into a cavity in a mammal body, to maintain the relationship of the tubing in the body when desired but upon choice, and to allow axial movement of and possible rotation of the elongated tubing (104) into or out of the device and mammal's interior cavity.

Planar field (102) may be a simple wide adhesive tape or a foam-backed tape as is currently used in a variety of instances in surgical procedures. The planar field may be air permeable if so desired. Attached to planar field (102) is stationary or fixed support (105) which may comprise an adherent member (106) and a base support (108). Base support (108) is fixed to planar field (102) using adherent member (106). Adherent member (106) may be any pliable material suitable for fixing base support (108) to the planar field (102).

Base support (108) typically will be constructed of a modestly firm polymer such as in NYLON, polyethylene, polypropylene, polyurethane, or any of the other materials commonly used in such devices. It must be of a type which is readily sterilizable and easily formed. The need for easy forming is more a matter of cost than a matter of criticality for this invention. The upper end of base support (108) meshes with adjustment member (110). In this variations as adjustment member (110) is twisted, the elongate tubing (104) is either loosened or tightened. As may be apparent from the drawing in FIG. 1, the planar field will hold the rest of the device in a specific relationship with the aperture in the mammal body. It should prevent axial movement of the elongate tubing (104) in and out of the body and because it does not use sutures to secure the elongate tubing (104) to the skins, the chance for infection and irritation is lessened.

Figure 2:
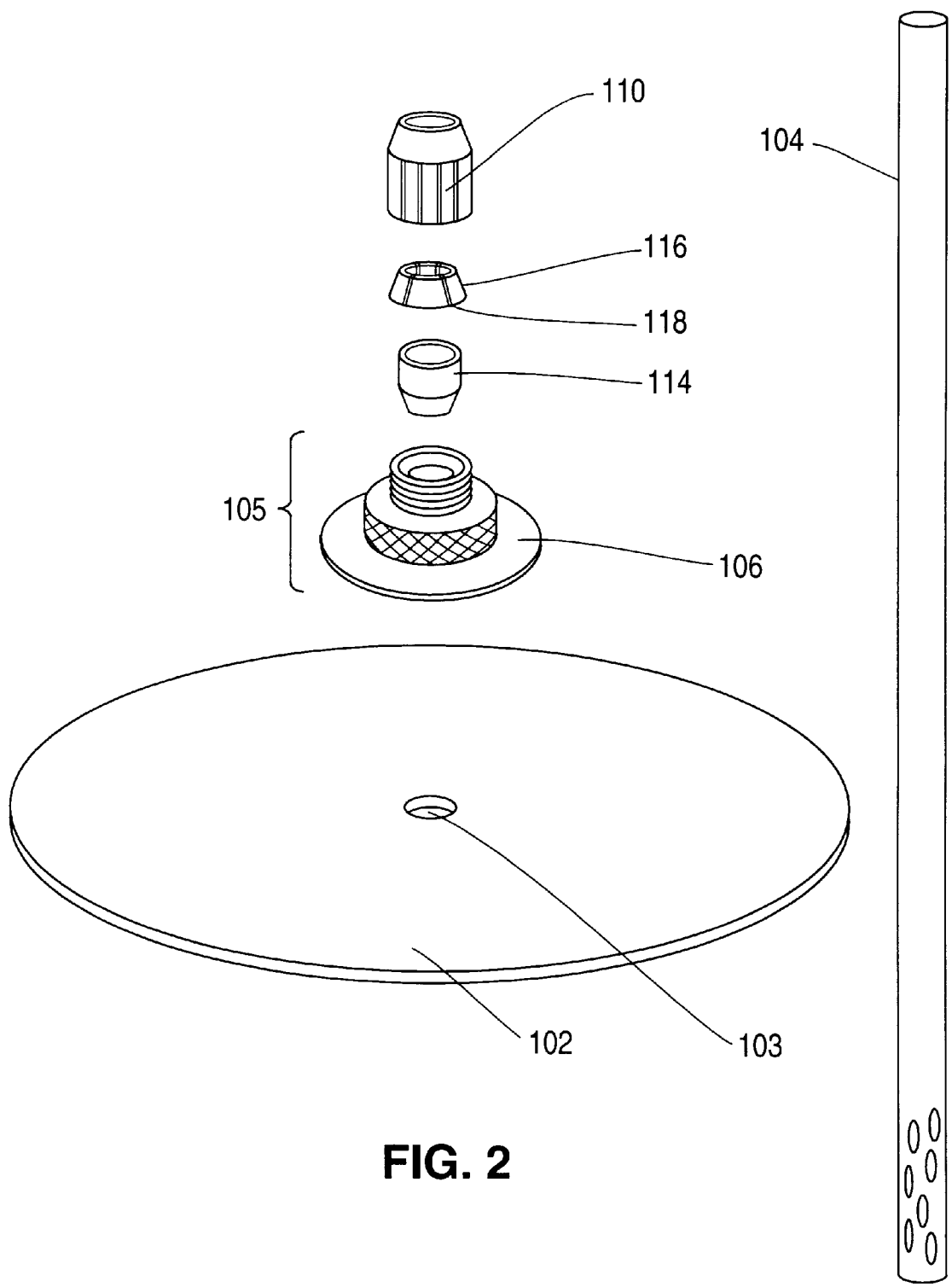
FIG. 2 shows a blow-up of the FIG. 1 device.

FIG. 2 shows the FIG. 1 variation of the device (100) in its component parts. Specifically shown are the planar field (102) with its included aperture (103). Also shown is the fixed support member (105) with its constituent parts the adherent member (106) and the base support (108) shown in more detail. The base support is shown with threads (112) which meet with threads on the interior of adjustment member (110). The threads on the interior of adjustment member (110) are not shown.

The upper end of base support (108) may have a conical shape surface on its interior. The conical interior surface of base support (108) allows the conical surface found on lower compression member (114) to mesh therein. Similarly, upper compression member (116) has an upper conical face which fits interior to adjustment member (110). Either of upper or lower compression members (116/114) may be made of a pliable polymeric material, e.g. natural rubber, synthetic rubbers silicones, and other functionally equivalent materials, to allow compression of the axial passageway through at least one of the members so to squeeze on elongated tube (104) when the moveable compression member (110) is rotated in the proper way. Upper compression member (116) is shown with plurality of slots (118). When a compression member having such slots is used, it may be made out of pliable, rubbery material or of somewhat more firm polymer such as polyethylene or polypropylene. The slots allows the compression of the upper compression member with less force on adjustment member (110). The lower compression member (114) may be of the same design as upper compression member (116) if so desired.

Figure 3:
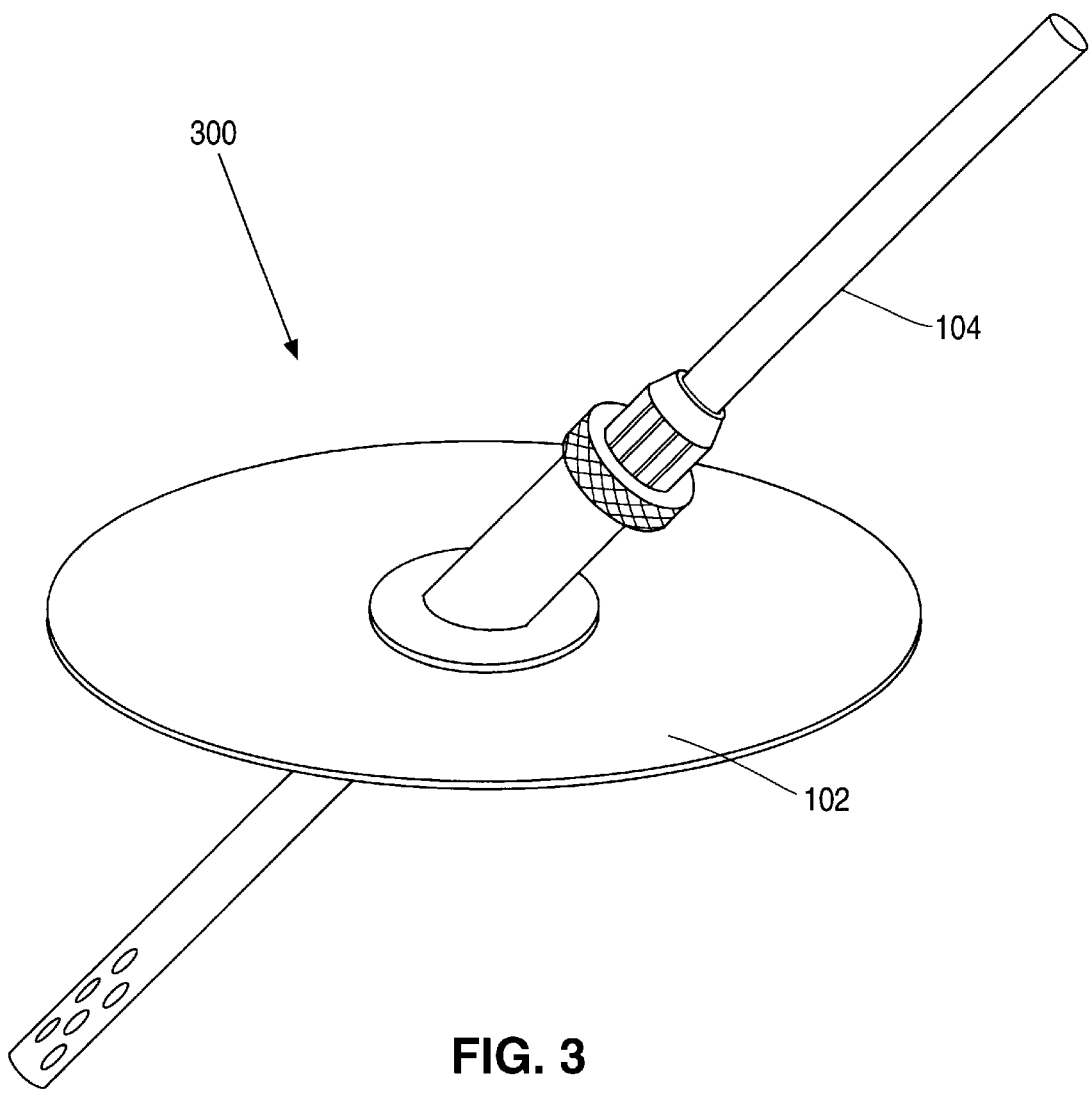
FIG. 3 shows a variation of the device in which the included tubing passes through at an angle.

FIG. 3 shows another variation of the inventive device (300) in which the elongate tube (104) passes through planar field (102) at an angle other than the 90° angle shown in the device of FIGS. 1 and 2. The variation (300) is otherwise quite similar to that shown in FIGS. 1 and 2.

Figure 4:
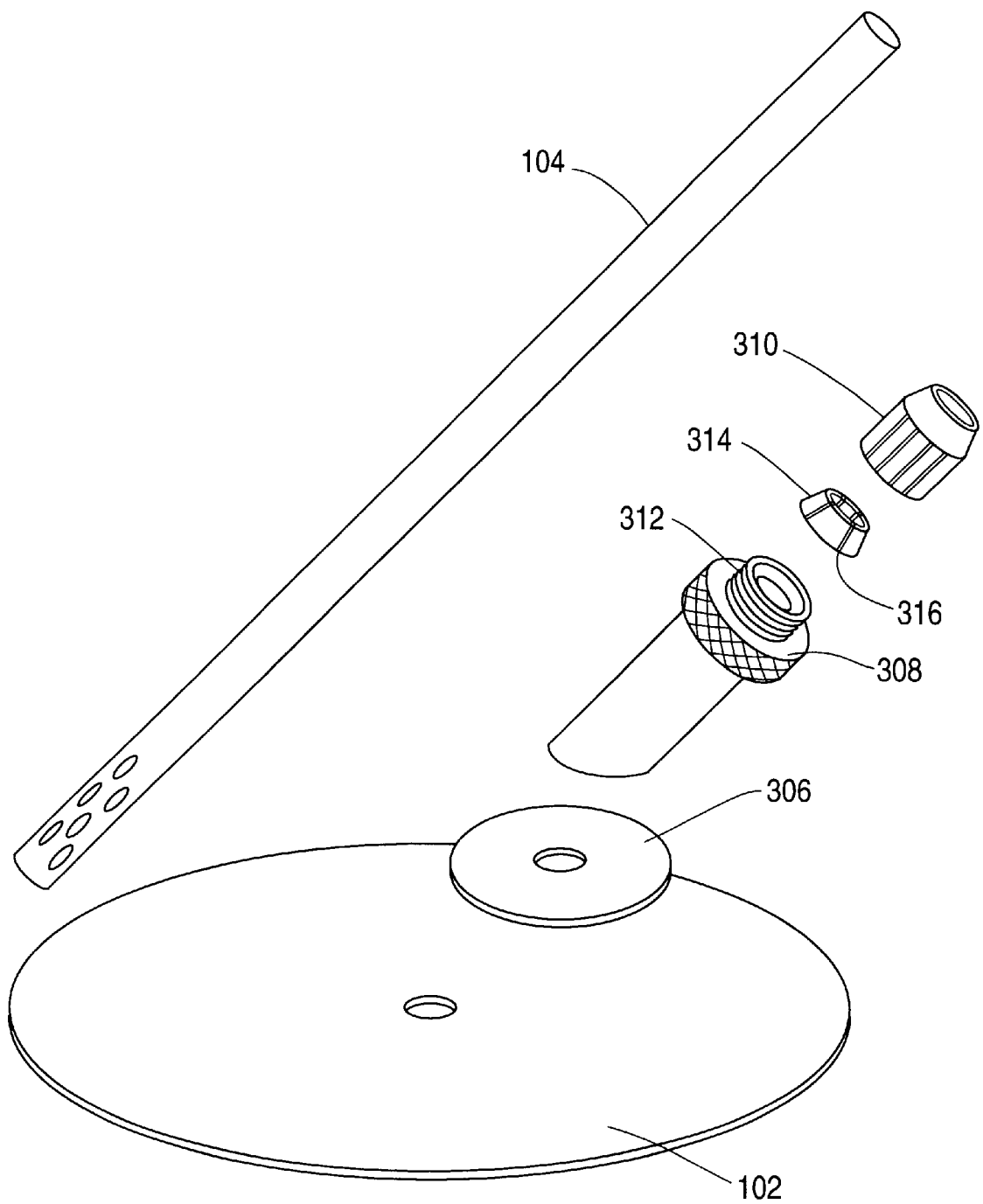
FIG. 4 shows a blow-up of the FIG. 3 device.

FIG. 4 shows a blow-up of the device having a planar field (102), elongate tubing (104), and the components making up the section which compresses elongate tube (104) and prevents it from moving. Those parts include the adherent member (306), base support (308), and adjustment member (310). Adherent member (106) serves the function of preventing movement of base support (308) in relation to planar field (102). Again, it has base support threads (312) on its upper outside periphery to allow cooperation with the threads which may be found on the interior of adjustment member (310). This variation is a bit different than that found in FIG. 1 because it involves use of only one compression member (314). Contained within the compression member are slots (316). As was the case with upper compression member (116) in FIG. 2, compression member (314) may be of a pliable, rubbery material or may be of material which is less flexible such as polyethylene or polypropylene. The slots (316) need not extend to the broad portion of the conical shape of compression member (314) so to form hinges which in cooperative relationship with a conical surface found in the upper, inner bore of base member (316) will squeeze down upon the axial bore through the compression member (314) when squeezed along its axis by adjustment member (310). Clearly, it is within the ambit of this invention that the positioning of compression member (314) may be the alternate event shown in FIG. 4, i.e., the base of the cone may be towards the base member (308) and not protrude into the axial passageway within that base member (308). In this variation the moveable adjustment member (310) would of necessity have a conical shaped inner surface to cooperate with the outer conical surface of compression member (314) to squeeze upon the inner bore and, in turn, compress onto the elongate tube (104).

This variation of a single compression member is available in any of the variations shown herein.

Figure 5:
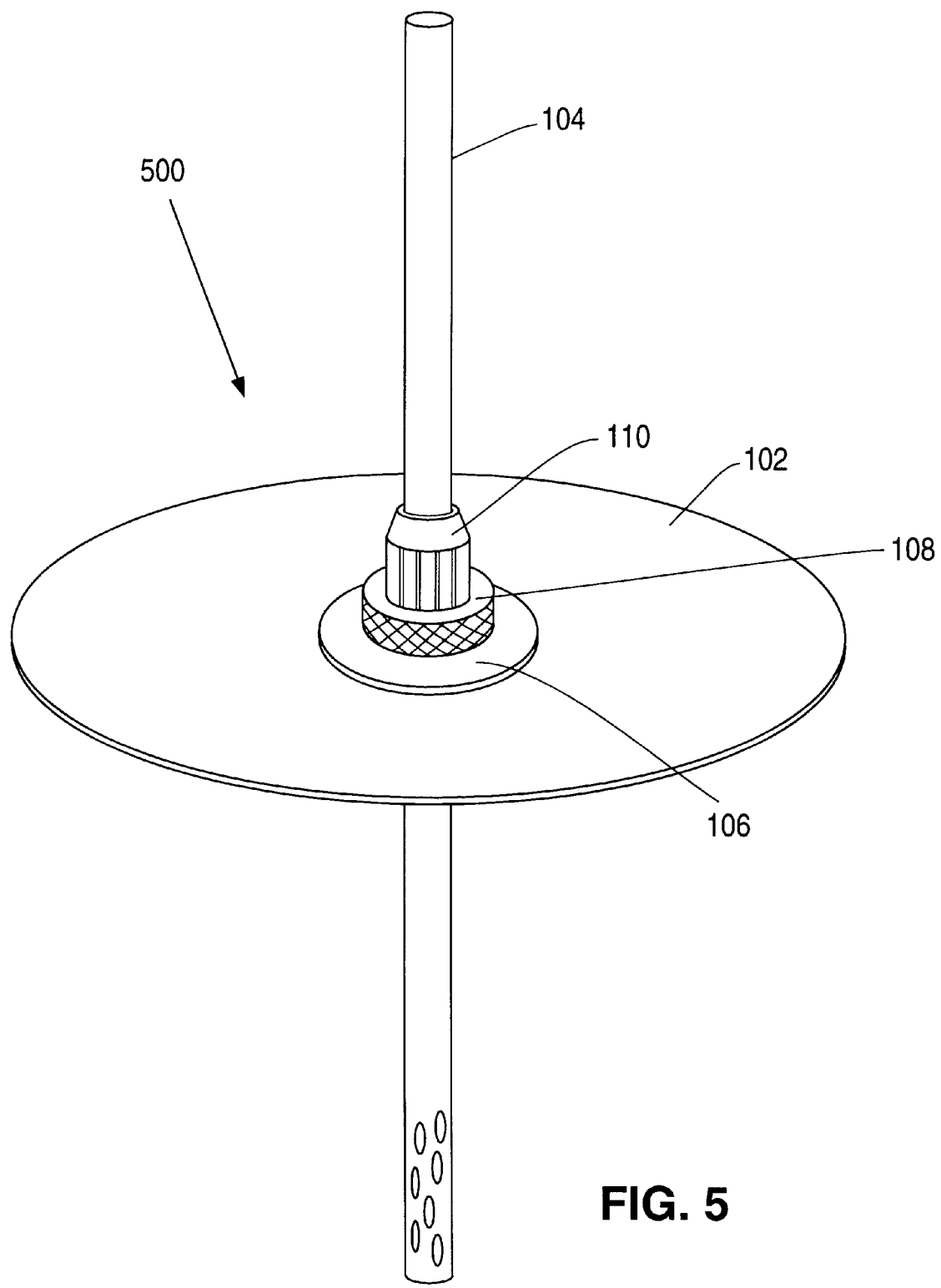
FIG. 5 shows further variation of the inventive device.

FIG. 5 shows another variation (500) of the inventive device. As was the case with the FIG. 1 and 2 variation, the variation has a planar field (102), a base support (108), an adjustment member (110), and an adherent member (106) to maintain elongate tubing (104) in a fixed but moveable position.

Figure 6:
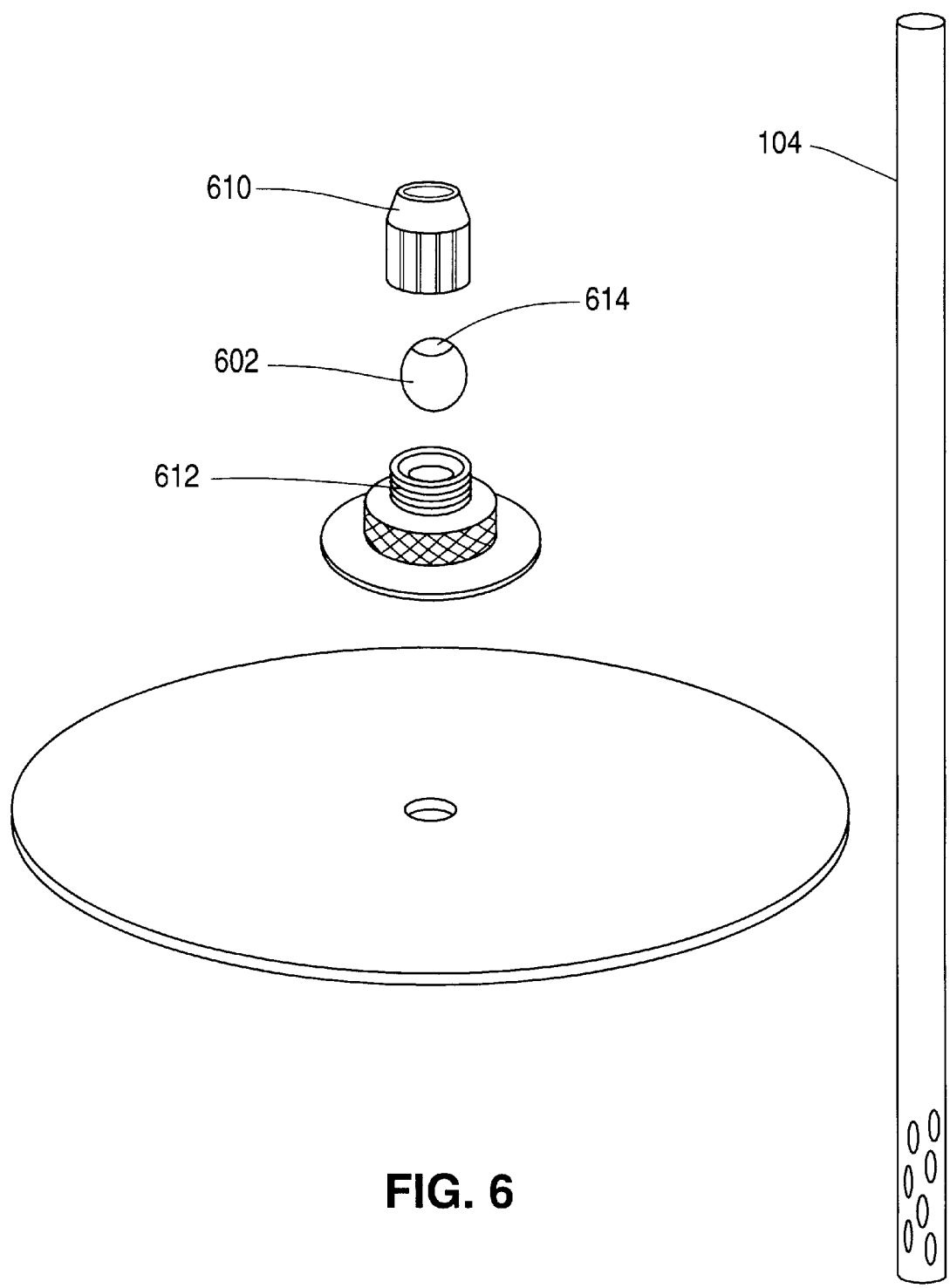
FIG. 6 shows a blow-up of the FIG. 5 device.

FIG. 6 shows an exploded view of the device found in FIG. 5. The major difference between this variation and the variations discussed in FIGS. 1–4 above, involve the use of a non-conical compression member. Specifically, in this instance, the compression member (602) is ovoid or spherical. The compression member (602) would cooperate with matching surfaces found on the interior of adjustment member (610) and base support (612). The compression member (602) may desirably be of a rubbery, compliant material, such as rubber, synthetic rubber, or polymeric silicone which upon squeezing by movement of the adjustment member (610) as it twisted down upon the threads found on base support (612) in turn squeezes its interior bore (614) and squeezes the elongate tube (104) which passes therethrough. This variation is to indicate that a wide variation of compression members may be used insofar as they allow the bore passing therethrough to compress when force is applied to the outer surfaces.

Figure 7:
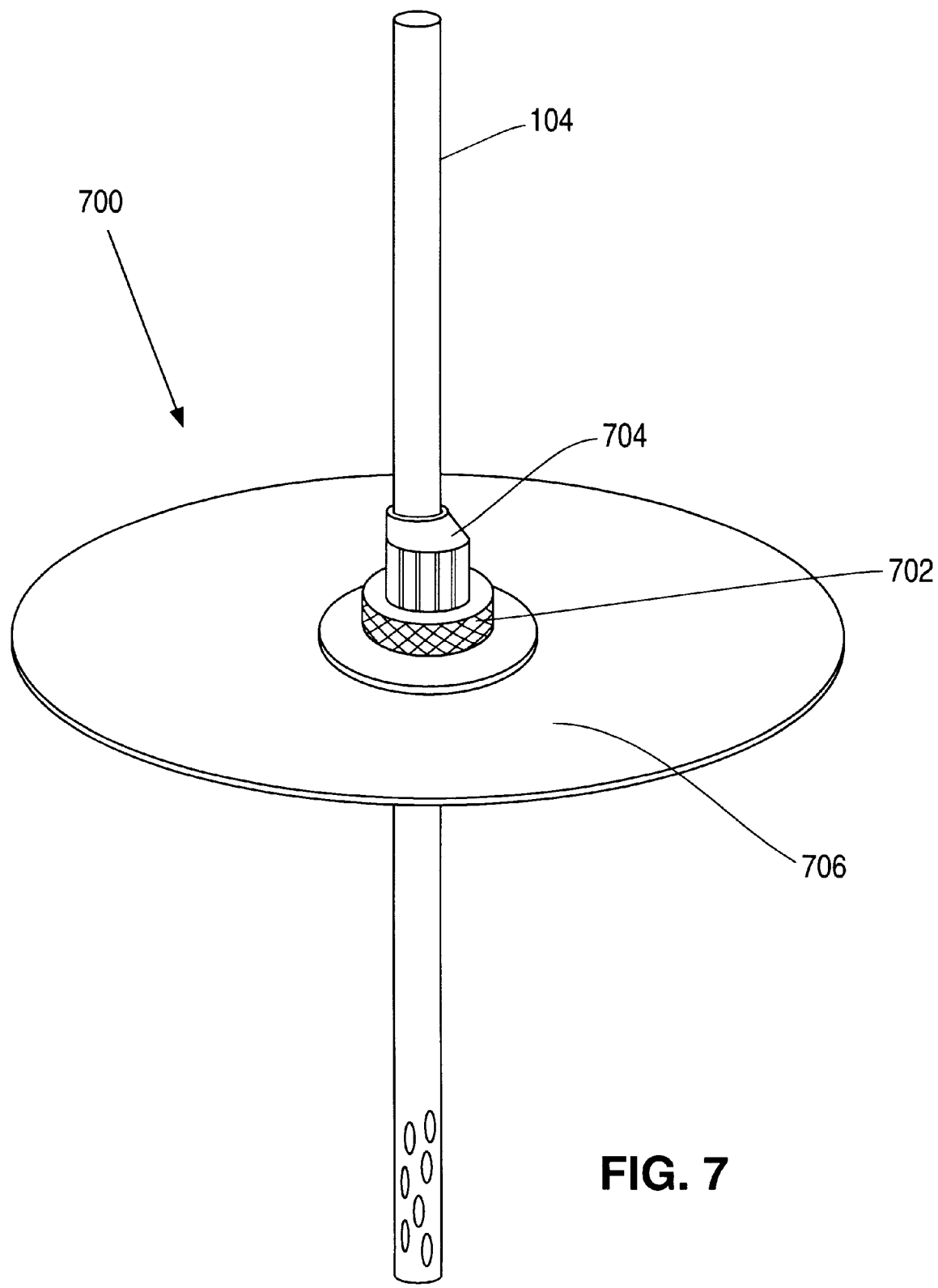
FIG. 7 shows a variation of the device using interference to maintain the elongate tubing passing therethrough in place.

FIG. 7 shows a further variation of the adjustable surgical retaining device (700). In this instance, the device (700) instead of using a compression member interior to the device uses interference between the base member (702) and the adjustment member (704) to affix the elongate tubing (104) in place. Otherwise the device is substantially as shown in the earlier figures.

Figure 8:
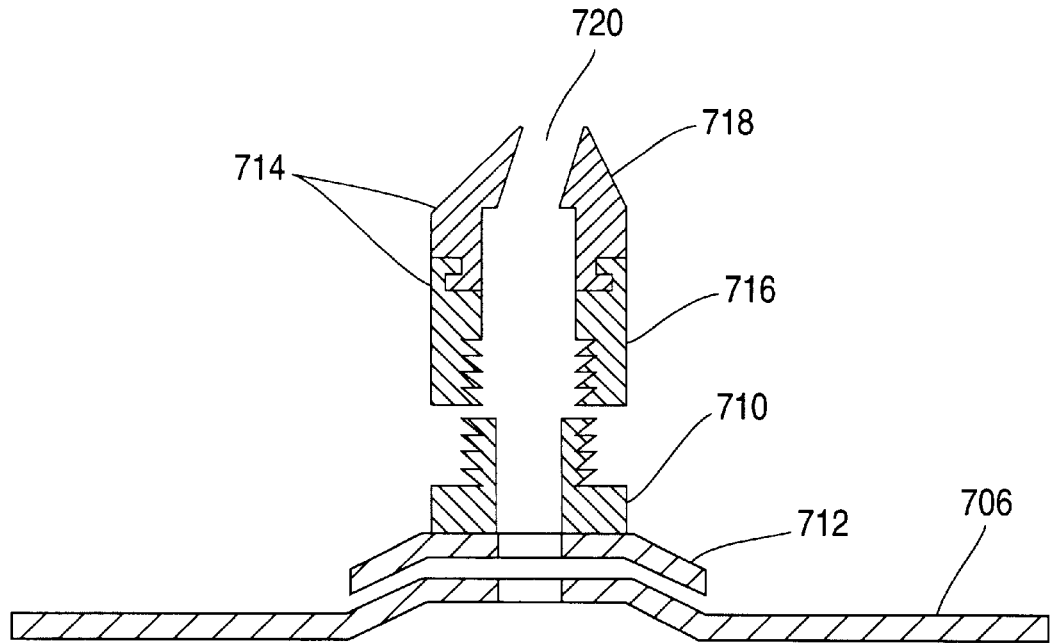
FIG. 8 is a side view cross-section of the FIG. 7 device.

FIG. 8 shows a cross section of the FIG. 7 device. There the planar field (706) having an aperture (708) is seen. In this variation, a dimple is found in the bottom side of the planar field (706) to allow packing of, e.g., a sealant containing perhaps an antibiotic. For instance, petroleum jelly containing a suitable antibiotic might be used when treating a pneumothorax to affectively seal the wound. This dimple may be used in any of the variations shown herein.

The base support (710) may include an adherent member (712) which has the same function as the adherent members mentioned above.

The adjustment member (714) in this variation may be two piece, although it need not be. The lower threaded section (716) is screwed on to the base member (710). It is desirably made so to rotate and yet allow the upper capped section (718) not to rotate. The orifice (720) which leaves to the top of cap (718) is angled in such a fashion that when (716) is screwed down tight that the axial passageway in base member (710) and the orifice in (720) meet at an angle. I have found that this angular meeting of the two passageways causes an interference fit when the elongate tubing (104) is pulled one way or the other through the passageways. It is difficult to move when snug tight. However, because of the upper cap (718) is rotatable, the tubing may be placed in any convenient position for placement as needed in conjunction with patient care on apparatus.

Figure 9:
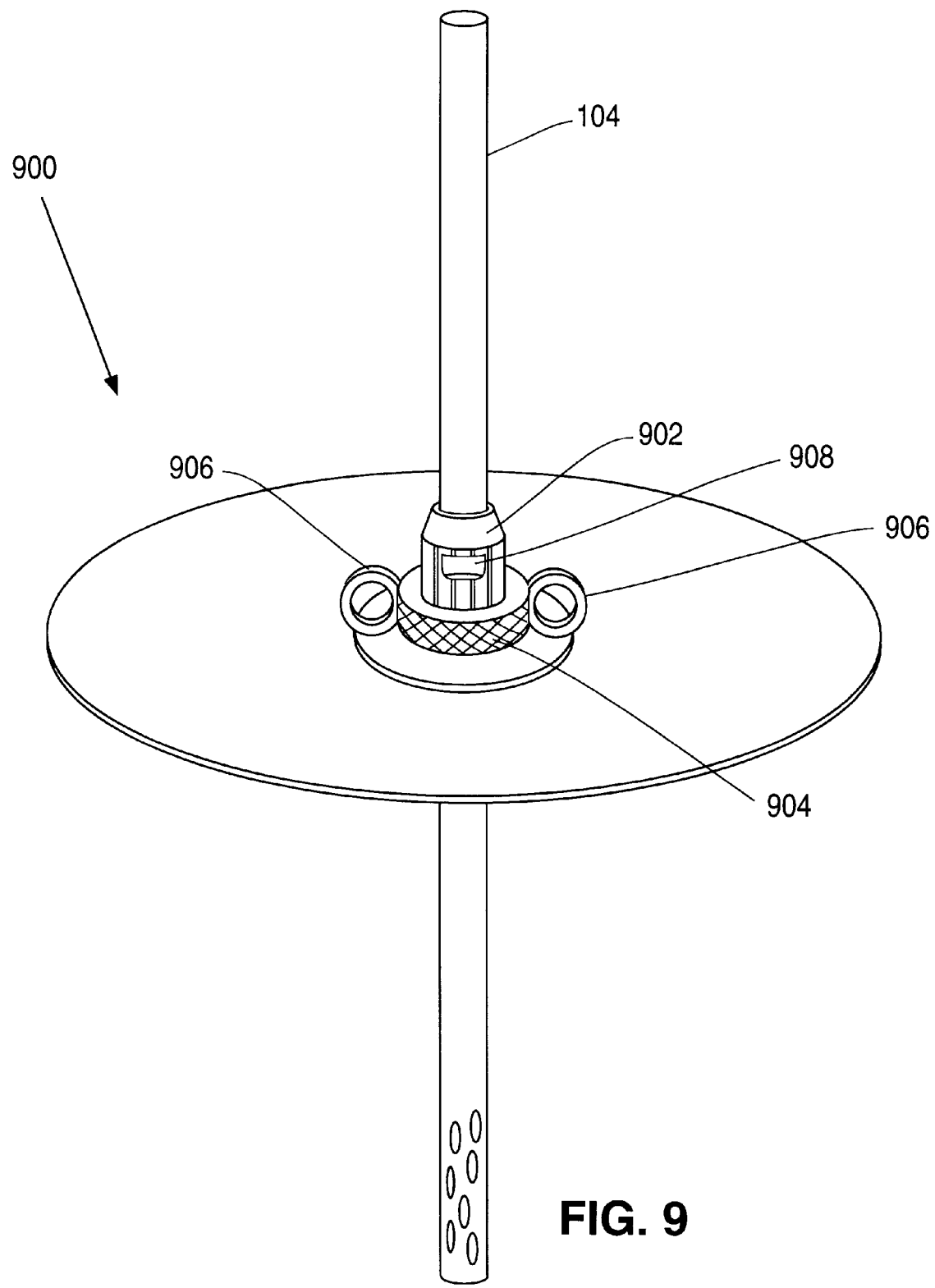
FIG. 9 shows a further variation of the inventive device.

FIG. 9 shows still another variation of the inventive device (900) in which the adjustment member (902) compresses elongate tubing (104) by compression but does so by axial movement of the compression member relative to the base support (904) rather than by twisting the adjustment member (902). In particular, the base support (104) has two finger grasp holds (906) through which a first and middle finger may be inserted. A thumb hole (908) is provided in the adjustment member. The adjustment member (908) releases the tubing by upward pressure on the thumb to extract the adjustment member (902) from base support (904) or entraps the elongate tubing (104) by squeezing the adjustment member (902) into the base support (904).

Figure 10:
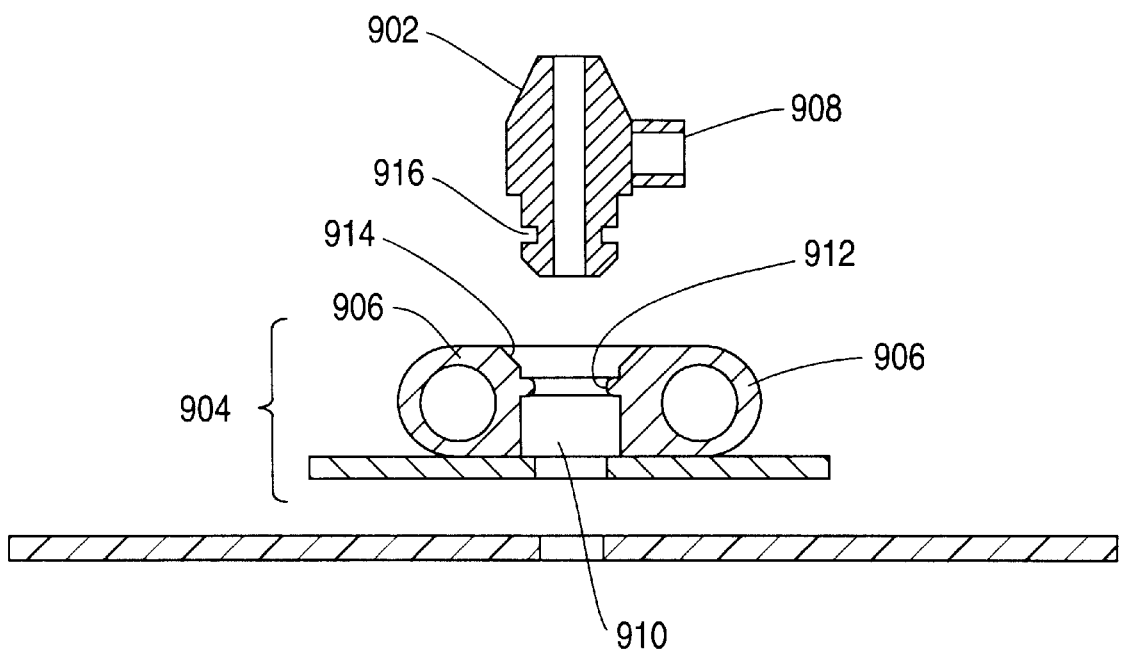
FIG. 10 shows a side view cross-section of the FIG. 9 device.

FIG. 10 shows the device (900) shown in FIG. 9 in cross section. In the cross section, the finger holds (906) may be seen as a portion of the base support (904). The interior bore (910) may be seen with its retainer ring (912) and its upper ramp region (914). The optional retainer ring (912) and the upper conical shaped ramp region (914) maybe used to cooperatively mesh with retainer groove (916) and ramp (918) found on adjustment member (902). Adjustment member (902) should be made of a material which upon insertion in the base member (904) compresses the inner actual bore therethrough to squeeze the elongate tubing passing thereto.

In operation, a physician or other health worker will place an index finger and a middle finger in a finger holds (906) and thumb in thumb hold (908). By squeezing the two together with the elongate tubing (104) placed in the bore of adjustment member (902), the ramp area (918) on adjustment member (906) will interact with ramp area (914) in the base member (904) and begin to constrict the inner bore of adjustment member (902). Upon additional pressure, the retainer ring (912) will slide over ramp (918) and into retainer groove (916). The elongate tubing (104) will be captured within the soft adjustment member (902).

The devices as noted above may be used for a wide variety of purposes which have also been discussed above. One particularly suitable use involves the treatment of pneumothorax and that treatment will be explained below in some more detail to allow a detailed understanding of the device and the way in which it is to be used. Although pneumothorax treatment is used as an example, it should be understood that the device may be used in any instance where a body lumen, cavity, or location is to be accessed by a tubing object or tubing such as a cannula, catheter, or other similar larger tubing devices. It may be used to protect the wound and lower the chance for infection.

Figure 11:
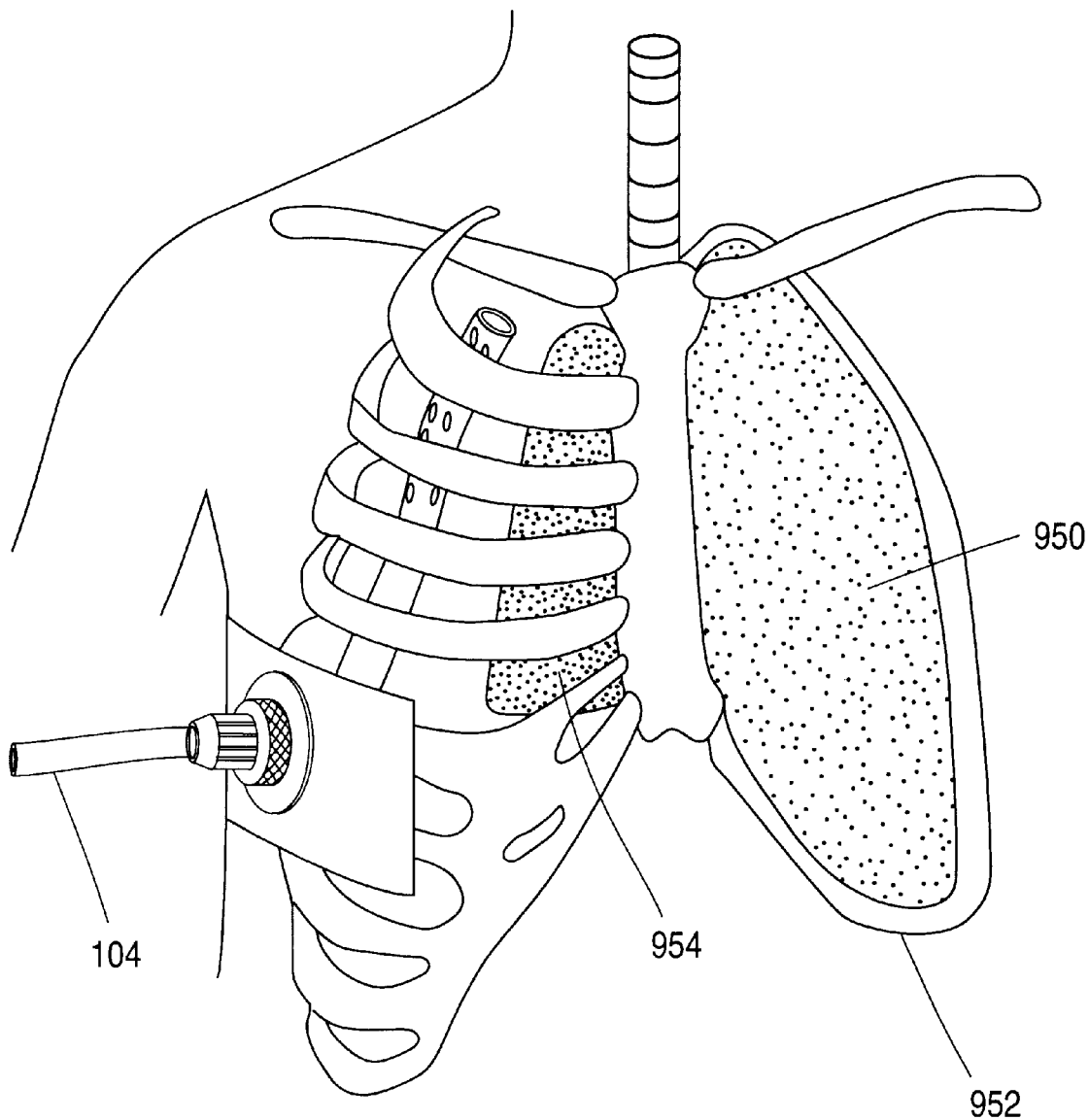
FIG. 11 shows the insertion of the inventive device into a human chest cavity.

FIG. 11 shows schematically a use of the device to treat a pneumothorax. In this drawing, the patient is shown without (variously) skin, muscles, and a portion of the rib cage. The patient's left lung (950) is shown to be fully inflated. The pleural sac (952) is also shown. The right lung (954) however is collapsed and is the cause of a pneumothorax The lung (954) has separated from the pleural sac and has shrunk to quite a small size. A previous treatment would include introduction of the elongate tube as discussed above—here called a chest tube—under aseptic techniques to reduce the potential for infection. The area on the chest is cleaned with a disinfecting solution. Often, for cosmetic purposes and clinical efficiency, an area under the arm is chosen as the site to prevent visible scarring The area is prepped and draped. To access the apex of the chest cavity, the attending physician makes an incision in the chest wall between two ribs through the skin and subcutaneous tissue down to the muscular layer. The attending physician then spreads the incision and bluntly tunnels through the muscle tissue up over the rib and punctures through the parietal pleural lining. A pathway now exists from the atmosphere to the pleural space. The tunnel into the pleural space is then dilated to accommodate an appropriate size chest tube. The chest tube (104) is then inserted up to the apex or to some other appropriate position in the pleural space and is then fixed to the chest wall to prevent it from either axially migrating or falling out.

Previously the attending physical wrapped suture around the exposed portion of the chest tub and has stitched it to the chest wall in an area close to the insertion site. In the current instance, however, one of the devices shown herein is slipped over the chest tube, the adhesive backing peeled off, and the adhesive may then be attached firmly to the chest or underarm skin. It is desirable to pack the wound with petroleum jelly or the like having a topical antibiotic in order to prevent infection prior to attaching the planar field to the skin.

As needed, the adjustment member may be loosened, the chest tube moved in or out or rotated, and the adjustment member retightened.

This device has the following advantages during use The chest tube may be easily repositioned without removing the fixation device. The device uses comfortable, non-irritating adhesive to adhere to the chest wall rather than sutures. The device is relatively tamper proof to prevent the patient from manipulating or inadvertently removing or loosening the seal and possibly even removing the chest tube. It is within the scope of this invention that the device have a locking mechanism similar to that used on other medical devices such as medication, bottles.

Finally, the collar or base support used in this device can be made of such a size that the strain normally placed on a wound by sutures and a tube is distributed around the chest. This substantially lowers the amount of irritation found at the wound site.

Having thus described the invention and provided examples showing how to use the invention, it should be apparent to those having ordinary skill in this art that variations exist in the device itself and within the method of using it. These variations would be within the spirit of the invention as outlined by the claims expressed below.

I claim as my invention:

1. An adjustable percutaneous access, fixation, and positioning device comprising, in combination:
   a.) a flexible planar field having an adhesive side for mounting against the skin, an exterior side opposite the adhesive side, and having an aperture through the planar field between the adhesive and exterior sides, and
   b.) a fitting assembly having a passageway therethrough suitable for slidably and adjustably accepting a tubular member passing between the adhesive and exterior sides of the planar field, which fitting assembly comprises a fixed support smaller than the planar field fixedly attached to the planar field and having exterior threads and an interior forming a portion of said passageway, said fitting assembly further comprising a rotatable threaded jam having interior threads cooperatively engaging the fixed support exterior threads, a tapered interior surface area above said interior threads, and an interior conduit surface forming a portion of said passageway, and further comprising a compression member for compressing said tubular member passing therethrough when said rotatable threaded jam is rotated with respect to the fixed support and in which the passageway aligns the tubular member with the aperture in the planar field.

2. The access device of claim 1 where the planar field comprises a foam sheet.

3. The access device of claim 1 additionally comprising a packable recess disposed at the planar field aperture on the adhesive side.

4. The access device of claim 3 where said packable recess contains an antibiotic or other therapeutic material.

5. The access device of claim 1 where the compression member comprises a conical member having an axial passageway for passage of the tubular member.

6. The access device of claim 5 where the conical member having an axial passageway for passage of the tubular member is split into sectors along the axis.

7. The access device of claim 1 where the compression member comprises an ovoid slip member having an axial passageway for passage of the tubular member.

8. The access device of claim 7 where the fitting comprises a fixed support having an axial passageway for passage of the tubular member and a rotatable member also having an axial passageway for passage of the tubular member which rotatable member which member is in alignment with the axial passageway in the fixed support and which, upon rotation, misaligns the two passageways to engage the tubular member.

9. The access device of claim 1 where the passageway in the fitting assembly is approximately perpendicular to the planar field.

10. The access device of claim 1 where the passageway in the fitting assembly is not perpendicular to the planar field.

11. The access device of claim 10 where the passageway in the fitting assembly is approximately 45 degrees to the planar field.

12. The access device of claim 1 where the fixed support is larger in diameter when measured in the plane of the planar field than the rotatable threaded jam.

13. A chest tube access, fixation, and positioning device comprising, in combination:

a.) a flexible planar field having an adhesive side for mounting against the skin, an exterior side opposite the adhesive side, and having an aperture through the planar field between the adhesive and exterior sides, and b.) a fitting assembly having a passageway therethrough suitable for slidably and adjustably accepting a chest tube passing between the adhesive and exterior sides of the planar field, which fitting assembly comprises a fixed support smaller than the planar field which is fixedly attached to the planar field and having exterior threads and an interior forming a portion of said passageway, a rotatable threaded jam having interior threads cooperatively engaging the fixed support exterior threads, a tapered interior surface area above said interior threads, and an interior conduit surface forming a portion of said passageway, a compression member for compressing a chest tube passing therethrough when said rotatable threaded jam is rotated with respect to the fixed support, and in which the passageway aligns the chest tube with the aperture in the planar field.

14. A method for the affixing and retaining a tube to the human body comprising the steps of:

providing an adjustable percutaneous access, fixation, and positioning device which comprises:
   a) a flexible planar field having an adhesive side for mounting against the skin, an exterior side opposite the adhesive side, and an aperture through the planar field between the adhesive and exterior sides, and
   b) a fitting assembly having a passageway therethrough suitable for slidably and adjustably accepting a tube passing between the adhesive and exterior sides of the planar field, said fitting assembly comprising a fixed support smaller than the planar field fixedly attached to the planar field and having exterior threads and an interior forming a portion of said passageway; a rotatable threaded jam having interior threads cooperatively engaging the fixed support exterior threads, a tapered interior surface area above said interior threads, and an interior conduit surface forming a portion of said passageway; and a compression member for compressing the tube passing therethrough when said rotatable threaded jam is rotated with respect to the fixed support and in which the passageway aligns the tube with the aperture in the planar field, inserting a tube having a proximal end and a distal end into an opening in the human body, positioning the adjustable percutaneous access, fixation, and positioning device such that the proximal end of the tube passes through the fitting passageway, passing the device along the tube until the adhesive side of the planar field contacts and adheres to the human body, and adjusting said fitting assembly to adjustably fix the tube in position within said fitting assembly.

15. The method of claim 14 further comprising the step of providing an antibiotic or medication to a recess provided on the adhesive side of the planar field prior to allowing the adhesive to adhere to the body.

16. The method of claim 14 in which the angle of the passageway is approximately perpendicular to the body.

17. The method of claim 14 in which the angle of the passageway is not perpendicular to the body.

18. A chest tube access, fixation, and positioning device comprising, in combination:

a.) a flexible planar field having an adhesive side for mounting against the skin, an exterior side opposite the adhesive side, and having an aperture through the planar field between the adhesive and exterior sides, and b.) a chest tube with a proximal end and a distal end, said distal end having apertures located therethrough, and c.) a fitting assembly having a passageway therethrough suitable for slidably and adjustably accepting a chest tube passing between the adhesive and exterior sides of the planar field, which fitting assembly comprises a fixed support smaller than the planar field which is fixedly attached to the planar field and having exterior threads and an interior forming a portion of said passageway, a rotatable threaded jam having interior threads cooperatively engaging the fixed superior exterior threads, a tapered interior surface area above said interior threads, and an interior conduit surface forming a portion of said passageway, a compression member for compressing said chest tube passing therethrough when said rotatable threaded joint is rotated with respect to the fixed member, and in which the passageway aligns the chest tube with the aperture in the planar field.

19. The access device of claim 18 where the planar field comprises a foam sheet.

20. The access device of claim 18 additionally comprising a packable recess disposed at the planar field aperture on the adhesive side.

21. The access device of claim 20 where said packable recess contains an antibiotic or other therapeutic material.

22. The access device of claim 18 where the compression member comprises a conical member having an axial passageway for passage of said chest tube.

23. The access device of claim 22 where the conical member having an axial passageway for passage of said chest tube is split into sectors along the axis.

24. The access device of claim 18 where the compression member comprises an ovoid slip member having an axial passageway for passage of said chest tube.

25. The access device of claim 24 where the fitting assembly comprises a fixed support having an axial passageway for passage of said chest tube and a rotatable member also having an axial passageway for passage of said chest tube which rotatable member which member is in alignment with the axial passageway in the fixed support and which, upon rotation, misaligns the two passageways to engage said chest tube.

26. The access device of claim 18 where the passageway in the fitting assembly is approximately perpendicular to the planar field.

27. The access device of claim 18 where the passageway of said fitting assembly is not perpendicular to the planar field.

28. The access device of claim 27 where the passageway of said fitting assembly is approximately 45 degrees to the planar field.

29. The access device of claim 18 where a portion of the fixed support is larger in diameter when measured in the plane of the planar field than the rotatable threaded jam.

30. An adjustable percutaneous access, fixation, and positioning device comprising, in combination:

a.) a flexible planar field having an adhesive side for mounting against the skin, an exterior side opposite the adhesive side, and having an aperture through the planar field between the adhesive and exterior sides, b.) a fitting assembly having a passageway therethrough suitable for slidably and adjustably accepting a tubular member passing between the adhesive and exterior sides of the planar field, which fitting assembly comprises a fixed support smaller than the planar field fixedly attached to the planar field and having exterior threads and an interior forming a portion of said passageway, said fitting assembly further comprising a rotatable threaded jam having interior threads cooperatively engaging the fixed support exterior threads, a tapered interior surface area above said interior threads, and an interior conduit surface forming a portion of said passageway, and further comprising a compression member for compressing said tubular member passing therethrough when said rotatable threaded jam is rotated with respect to the fixed support and in which the passageway aligns the tubular member with the aperture in the planar field, and c.) said tubular member cooperatively passing through said passageway of said fitting assembly and being adjustably engaged by said passageway.

31. The access device of claim 30 wherein said tubular member comprises a chest tube with a proximal end and a distal end, said distal end having apertures located therethrough.

* * * * *